United States Patent
Tashenov

(10) Patent No.: US 11,350,898 B2
(45) Date of Patent: Jun. 7, 2022

(54) APPARATUS AND METHOD FOR CONTROLLING AN X-RAY DEVICE DURING AN INTERVENTION PROCEDURE

(71) Applicant: Siemens Healthcare GmbH, Erlangen (DE)

(72) Inventor: Stanislav Tashenov, Heroldsbach (DE)

(73) Assignee: Siemens Healthcare GmbH, Erlangen (DE)

( * ) Notice: Subject to any disclaimer, the term of this patent is extended or adjusted under 35 U.S.C. 154(b) by 203 days.

(21) Appl. No.: 16/695,808

(22) Filed: Nov. 26, 2019

(65) Prior Publication Data

US 2020/0170752 A1 Jun. 4, 2020

(30) Foreign Application Priority Data

Nov. 30, 2018 (DE) .......................... 102018220758.5

(51) Int. Cl.
*A61B 6/00* (2006.01)
*A61B 90/90* (2016.01)
*A61B 90/00* (2016.01)

(52) U.S. Cl.
CPC ................ *A61B 6/504* (2013.01); *A61B 6/54* (2013.01); *A61B 6/542* (2013.01); *A61B 6/547* (2013.01); *A61B 90/90* (2016.02); *A61B 2090/0811* (2016.02)

(58) Field of Classification Search
CPC .......... A61B 6/504; A61B 6/54; A61B 6/542; A61B 6/545; A61B 6/547
USPC ............................................ 378/62, 162–165
See application file for complete search history.

(56) References Cited

U.S. PATENT DOCUMENTS

| | | | | |
|---|---|---|---|---|
| 5,282,254 A | * | 1/1994 | Chiu | A61B 6/06 378/159 |
| 5,369,678 A | * | 11/1994 | Chiu | A61B 6/06 378/152 |
| 7,010,080 B2 | * | 3/2006 | Mitschke | A61B 6/12 378/15 |
| 7,590,442 B2 | * | 9/2009 | Boese | A61B 6/12 378/62 |
| 7,930,014 B2 | * | 4/2011 | Huennekens | A61B 6/487 600/407 |

(Continued)

FOREIGN PATENT DOCUMENTS

DE 102006011255 A1 9/2007
JP 2010158303 A 7/2010

(Continued)

OTHER PUBLICATIONS

An English translation of DE 10 2006 011 255 A1 by Patent Translate.*

(Continued)

*Primary Examiner* — Allen C. Ho
(74) *Attorney, Agent, or Firm* — Lempia Summerfield Katz LLC

(57) ABSTRACT

Systems and methods are provided for controlling an x-ray device with an introducer sheath configured to for introduce an intervention device into a vessel and an acquisition facility for automatically acquiring an item of identification information of the intervention device and for generating a corresponding item of control information for the x-ray device. The acquisition facility is arranged directly on the introducer sheath.

19 Claims, 2 Drawing Sheets

(56) References Cited

U.S. PATENT DOCUMENTS

| | | | | |
|---|---|---|---|---|
| 7,988,633 B2* | 8/2011 | Hossack | ............... | A61B 8/4472 |
| | | | | 600/467 |
| 8,586,932 B2* | 11/2013 | Rousso | ................. | G01T 1/161 |
| | | | | 250/363.04 |
| 8,594,271 B2* | 11/2013 | Sakaguchi | ................ | G06T 7/11 |
| | | | | 378/4 |
| 8,600,478 B2* | 12/2013 | Verard | ................... | A61B 90/90 |
| | | | | 600/424 |
| 8,852,208 B2* | 10/2014 | Gomez | .................... | H01F 5/04 |
| | | | | 606/130 |
| 9,095,308 B2* | 8/2015 | Florent | .................. | A61B 6/488 |
| 9,415,195 B2* | 8/2016 | Schreck | ............. | A61M 25/104 |
| 9,439,606 B2* | 9/2016 | Schmitt | .................. | A61B 6/032 |
| 9,713,451 B2* | 7/2017 | Auvray | .................. | A61B 6/487 |
| 9,775,538 B2* | 10/2017 | Eichler | ................ | A61B 8/4245 |
| 9,936,859 B2* | 4/2018 | Ebata | ............... | A61B 17/00234 |
| 10,152,788 B2* | 12/2018 | Klaiman | .............. | A61B 6/5211 |
| 10,188,362 B2* | 1/2019 | Sato | ..................... | A61B 6/5205 |
| 10,542,954 B2* | 1/2020 | Spencer | ................. | A61B 6/504 |
| 10,568,585 B2* | 2/2020 | Anderson | .............. | A61B 6/504 |
| 10,631,806 B2* | 4/2020 | Nambu | .................. | A61B 6/481 |
| 10,667,775 B2* | 6/2020 | Anderson | ............ | G16H 20/40 |
| 10,733,753 B2* | 8/2020 | Furuichi | ............... | A61B 6/541 |
| 10,758,190 B2* | 9/2020 | Anderson | ................ | A61B 8/12 |
| 10,799,775 B2* | 10/2020 | Sargent | ............. | A63B 53/0466 |
| 10,806,421 B2* | 10/2020 | Keller | ....................... | A61B 8/12 |
| 10,856,825 B2* | 12/2020 | Dargis | ...................... | A61B 6/54 |
| 10,973,481 B2* | 4/2021 | Yoshida | ................ | A61B 6/5235 |
| 10,980,498 B2* | 4/2021 | Sato | ..................... | A61B 6/5264 |
| 11,026,648 B2* | 6/2021 | Mielekamp | ............ | A61B 6/469 |
| 11,058,386 B2* | 7/2021 | Shima | ..................... | A61B 6/12 |
| 11,071,505 B2* | 7/2021 | Schaefer | ................. | A61B 6/12 |
| 11,138,697 B2* | 10/2021 | Dargis | ................... | A61B 6/463 |
| 2013/0261439 A1 | 10/2013 | Schmitt et al. | | |
| 2015/0119639 A1 | 4/2015 | Ebata | | |
| 2018/0014852 A1 | 1/2018 | Gomez et al. | | |
| 2018/0042514 A1 | 2/2018 | Verard | | |

FOREIGN PATENT DOCUMENTS

| | | |
|---|---|---|
| JP | 2013544612 A | 12/2013 |
| JP | 2014018232 A | 2/2014 |
| JP | 2017153973 A | 9/2017 |
| JP | 2018033818 A | 3/2018 |

OTHER PUBLICATIONS

An English translation of JP2018033818A by Patent Translate.*
An English translation of JP2014018232A by Patent Translate.*
German Office Action for German Application No. 10 2018 220 758.5 dated Sep. 23, 2019.
Japanese Office Action for Japanese Application No. 2019-190637 dated Feb. 2, 2021, with English translation.

* cited by examiner

APPARATUS AND METHOD FOR CONTROLLING AN X-RAY DEVICE DURING AN INTERVENTION PROCEDURE

CROSS REFERENCE TO RELATED APPLICATIONS

This application claims the benefit of DE 102018220758.5, filed on Nov. 30, 2018, which is hereby incorporated by reference in its entirety.

FIELD

Embodiments relate to an apparatus and method for controlling an x-ray device.

BACKGROUND

If a catheter is placed in a patient, for example, the catheter is introduced into the corresponding vessel of the patient by an introducer sheath. The tip of the catheter may be observed by an x-ray device to be able to continuously ascertain its exact position. Aside from the simple catheter there are other intervention devices, such as guide wires, guide catheters, stents, recording devices etc., that may be introduced into the patient by way of the introducer sheath.

The visibility of the intervention devices on x-ray images is dependent on the operating parameters of the x-ray source, for example, the focal distance, the tube voltage, the tube current, the pulse width and the thickness of the copper filter. The operating parameters are selected optimally for each clinical situation on the basis of the induced organ program (OGP).

With automatic exposure controls the organ programs define the intervention device (and the corresponding clinical situation) by its material, size, and speed. The organ programs also define the desired visibility (IQ) or its level for the intervention device and thus also the x-ray dose required for the patient. To achieve an x-ray dose as low as reasonably achievable (ALARA) for the patient, the visibility of the device may be kept to a minimal level that only just allows for the clinical procedure. For example, with the navigation with guide wires, a significantly lower visibility and lower resolution is necessary compared with the positioning of a stent, with which very high visibility and resolution are required. Furthermore, the optimal image processing may differ significantly with different intervention devices. Each device requires a dedicated organ program or a series of organ programs in the respective clinical situation.

Automatic exposure controls in respect of a contrast-to-noise ratio are relatively simple to parameterize for each specific intervention device. Each device receives its own organ program in a defined clinical situation. As a result, the number of organ programs may increase significantly compared with the current situation.

In order to achieve the ALARA working conditions, the user has to toggle between the organ programs each time the user changes the intervention device. With a typical intervention, the user frequently changes the intervention devices. This requires continuous interaction with the system, that additionally demands time and attention. The majority of users do not toggle between the organ programs during an intervention, however. An automatic system that selects or sets the respective optimal organ program is desirable. An automatic system of this type is currently not available. This results in unnecessarily high x-ray doses for the patient during the intervention and/or in an inadequate image quality.

The program of automatically adjusting the organ programs or parameters of the x-ray device is increased as a result in that more and more organ programs are available. Its selection becomes increasingly difficult.

BRIEF SUMMARY AND DESCRIPTION

The scope of the present invention is defined solely by the appended claims and is not affected to any degree by the statements within this summary. The present embodiments may obviate one or more of the drawbacks or limitations in the related art.

Embodiments provide a device that allows the x-ray dose to be kept as low as possible while intervention devices are observed.

In an embodiment, an apparatus for controlling an x-ray device is provided that includes an introducer sheath for introducing an intervention device into a human vessel and an acquisition facility for automatically acquiring an item of identification information of the intervention device and for generating a corresponding item of control information for the x-ray device. The acquisition facility is arranged directly on the introducer sheath.

The apparatus provides control data for an x-ray device. The apparatus may generate control data to influence parameters of the x-ray device. The apparatus includes an introducer sheath, with which an intervention device may be introduced into a human vessel. An introducer sheath establishes an interface between the interior of the vessel and the outside world. The introducer sheath may be used to introduced catheters, wires, surgical instruments, diagnostic instruments, and suchlike (referred to below as intervention devices) from the outside into a vessel. Introducer sheaths of this type are also suited to introducing intervention devices into animal vessels.

The apparatus for controlling the x-ray device using an acquisition facility is configured to automatically acquire an item of identification information from the intervention device. The intervention devices may be classified or even identified individually using the identification information. One type or class of intervention devices may be catheters, for example. Where applicable the identification information is more detailed and specifies whether a guide catheter, a small catheter with a stent, a microcatheter, or suchlike is used. The identification information specifies, in the respectively desired depth of detail, a type of intervention device or an individual piece that is involved.

The acquisition facility acquires the identification information and therefrom generates a corresponding item of control information for the x-ray device. In one case, the type information corresponds to the control information. For example, a catheter bears the identification information "1" and this "1" is forwarded to the x-ray device as control information to set the "organ program number 1", for example. The acquired identification information may also be converted into control information. Different types of intervention devices may call up the same control information or the same setting of the x-ray device. The identification information may be assigned to any item of control information by the acquisition facility.

The acquisition facility is arranged directly on the introducer sheath. For example, the acquisition facility may be fixedly connected to the introducer sheath, e.g. inseparably. The acquisition facility may be detachably fixed to the introducer sheath. The acquisition facility automatically acquires which type of intervention device is guided by the introducer sheath. The sensor system of the acquisition facility may be directed at the introduction channel of the introducer sheath. The type of intervention device may be automatically acquired and the x-ray device may be automatically controlled. The radiation parameters of the x-ray device may be adjusted automatically according to the type or individual of the intervention device. If situation-related minimal radiation intensities are assigned to the intervention devices, the x-ray dose may be kept as minimal as possible in the case of an intervention, for example, with a plurality of intervention devices.

In an embodiment, the apparatus also includes the intervention device and the intervention device includes the identification information at its distal end region. The distal end region of the intervention device corresponds, for example, to the catheter tip or the region that is firstly introduced into the vessel by the introducer sheath. The code may also be arranged in the vicinity of the catheter tip, if, for example, for improved x-ray visibility the outermost tip is coated with a heavy metal that would interfere with the code. In particular, the distal shaft portion of a catheter tube may include the identification information. The acquisition facility on the introducer sheath immediately identifies its type or identification symbol when the intervention device is introduced and may be controlled accordingly on the x-ray device already before intervention starts.

In an embodiment of the apparatus with the intervention device, the identification information may be attached to the intervention device by a magnetic or optical code, and the acquisition facility may magnetically or optically acquire the code. In the case of a magnetic code, a magnetic powder may be introduced into the case of the intervention device upon production, for example. A magnetic, positionally variable encoding may be used. A corresponding acquisition facility includes a magnetic sensor, such as a Hall probe for example. In the case of optical encoding, a barcode or a QR code may be attached, for example, imprinted, onto the intervention device (QR code=Quick Response code). The optical encoding may be arranged in a lower layer of the intervention device where the layers thereover are transparent. The corresponding acquisition facility includes a corresponding optical sensor system and may be a laser scanner, for example. A contactless scanning of the intervention device may be achieved by the magnetic or optical encoding in order to obtain the type information. Alternatively, the encoding may be carried out by integrating a miniaturized RFID chip in the region of the tip of the intervention device (RFID=radio-frequency identification). A corresponding device scanner then uses the RFID technology to identify the intervention device.

The acquisition facility may acquire at least one position marker of the intervention device and generate the control information as a function of the at least one position marker. An item of identification information of the intervention device and an item of position information may be obtained. Control of the x-ray device may thus be achieved not only on the basis of the identity of the intervention device but also on the basis of the position information. An additional degree of freedom is thus available to adjust the parameters of the organ program, for example, with respect to an intended image quality with as low a radiation dose as possible.

In an embodiment, the acquisition facility may take into account a position and/or speed and/or direction of movement of the intervention device for generating the control information on the basis of the at least one position marker. For example, the radiation exposure, but also other exposure parameters of the x-ray device, may be controlled as a function of the position of the intervention device. A low x-ray dose may be used when a catheter is introduced into the groin of a patient, for example, whereas in a target position region, when the catheter tip is located in the vicinity of the target, a high radiation exposure is desired.

The position information may also be used by the acquisition facility to determine a speed of the intervention device, for example. The contrast or another operating or exposure parameter of the x-ray device may be set as a function of the speed. A lower contrast may be set in a navigation phase of the intervention device than in an actual intervention phase, e.g. a positioning phase of a stent. Furthermore, the position information may also be used by the acquisition facility to determine a direction of movement of the intervention device and to control the x-ray device with the direction of movement information. For example, when a catheter is pulled out, a lower image quality (where applicable also the complete switch-off of the radiation) may automatically be set than when the catheter is inserted. Not only statistical but also dynamic parameters of the intervention device may be evaluated for the control of the x-ray device.

In an embodiment, the acquisition facility includes a laser scanner for acquiring optical codes on the intervention device. Laser scanners of this type are reliable and may be used as standard components. This may provide high safety when the x-ray device is controlled.

In an embodiment, the intervention device includes a catheter, a guide wire, a stent, and/or a surgical instrument. The intervention device may be a catheter with a stent or a catheter with a balloon, for example. Furthermore, the catheter may be a guide catheter, a microcatheter, or suchlike. The surgical instrument may be a cutting element, a clamping element, or suchlike. The x-ray device may be adjusted to the specific type or identity of the intervention device. If necessary, the radiation exposure or an exposure parameter, e.g. the focus, may be automatically adjusted specifically to a respective surgical instrument.

Furthermore, the intervention device may be optically transparent at least in one region and for the optical code may include a lower transparency compared with the one region. The transparency of the intervention device may be used if a number of intervention devices are introduced by the introducer sheath into the vessel. The transparency provides that the individual intervention devices are not concealed. The optical transparency relates to the acquisition facility and thus to the optical radiation that the acquisition facility uses. If the acquisition facility includes an infrared sensor for detecting the type of intervention device, for example, the intervention device may be transparent for the infrared radiation locally in regions. The same applies if the acquisition facility is operating in the visible region of the light.

In an embodiment, an x-ray device is provided that includes an apparatus, as has been described above. The apparatus is connected to a control facility of the x-ray device by data technology so that the control facility may obtain the identification information relating to the intervention device from the acquisition facility. The power supply to the acquisition facility is, where applicable, also provided by the control facility of the x-ray device. In some examples, the data transmission between the acquisition facility on the introducer sheath and the control facility of the x-ray device is carried out by a wireless data link.

Embodiments also provide a method for controlling an x-ray device by automatically acquiring an item of identification information of an intervention device directly on an introducer sheath for introducing an intervention device into a human vessel and generating an item of control information for the x-ray device that corresponds to the identification information.

The variation possibilities and advantages described in conjunction with the apparatus also apply analogously to the method.

The automatic acquisition may also include an acquisition of a position and/or a speed and/or a direction of movement of the intervention device by the introducer sheath, and the generation of the control information carried out as a function of the acquired position and/or speed and/or direction of movement. An item of statistical information with respect to the intervention device or an item of dynamic information relating to the movement of the intervention device may be acquired. The contrast of the x-ray recording may be increased, for example, if the intervention device is located in the vicinity of the target position or moves at a slower speed or toward the target. The contrast may be reduced, for example, if the intervention device is located further away from the target or moves at a higher speed or away from the target. All statistical and dynamic parameters may in some examples also be involved at the same time in the control of the x-ray device.

In an embodiment, one of several organ programs in the x-ray device is selected as a function of the control information. The control information generated as a function of the identification information is used to select the respective organ program with specific radiation parameters. For example, an intracardiac catheter program is selected if the acquisition facility detects that the catheter introduced by the introducer sheath is an intracardiac catheter.

An organ program with a lower x-ray dose may be automatically selected if the speed is above a threshold value, compared with an organ program that is selected at a speed below the threshold value. One individual parameter of the x-ray device as a function of the speed of the intervention device or a complete organ program that, in some examples, includes a plurality of individual parameters may be set. The radiation exposure, but also the focal length and/or exposure time or another parameter may be varied successively or continuously as a function of the speed.

An exposure parameter or display parameter of the x-ray device may be set on the basis of the control information. One such exposure parameter relates to the optical type of obtaining the x-ray image. For example, the contrast of the x-ray image or the video display may be changed or set by varying the radiation exposure or the focal length. The display parameter may be a parameter that provides a change in display by subsequent image processing. The display parameter may affect an increase in contrast or contour, but also influence a zoom factor. It is favorable, for example, to display a larger cutout of the observation region in the case of a high speed of the intervention device than with a lower speed of the intervention device. The exposure parameter may relate more to the hardware such as x-ray source, x-ray detector and suchlike, whereas the display parameter relates more to the software and the computational image processing. With the parameter, the control information obtained from the identification information of the intervention device may where applicable also be influenced simultaneously.

An acquired position of the intervention device may be fixed as a zero position and a relative position of the intervention device relative to the zero position to be displayed on the x-ray device or further processed in the x-ray device. A reference position, e. g. a zero position, may be fixed very accurately on the introducer sheath with the aid of acquisition. Other working positions, i.e. relative positions, may then relate to this reference position. A very reliable positioning is possible.

DETAILED DESCRIPTION

Figure 1:
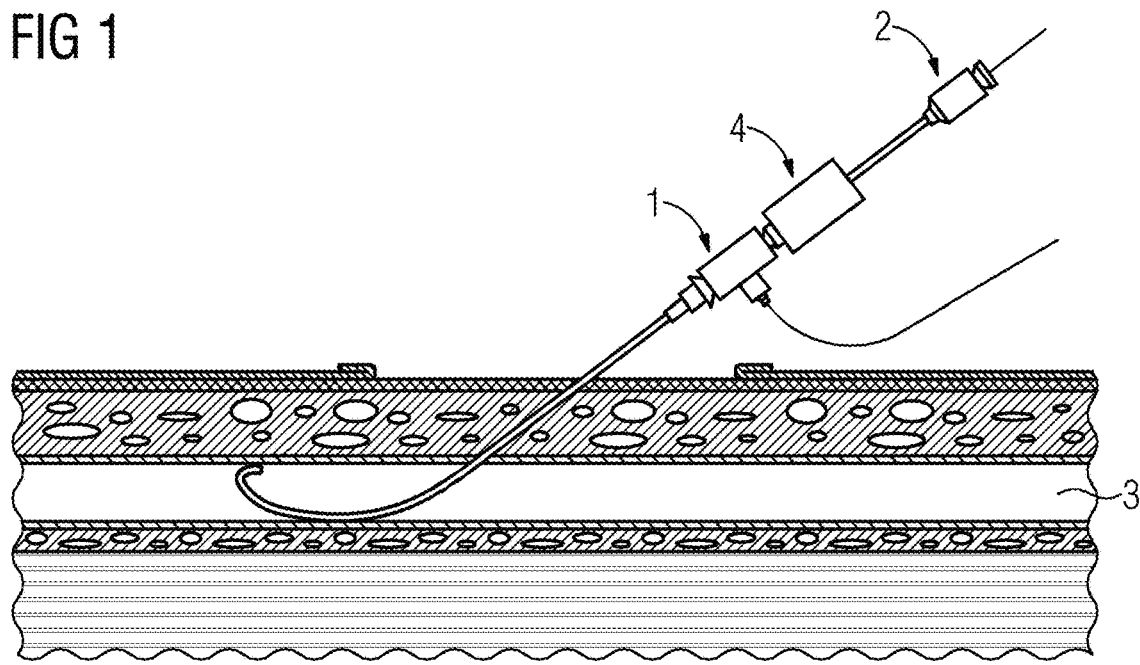
FIG. 1 depicts an apparatus with introducer sheath and acquisition facility in use according to an embodiment.

FIG. 1 depicts an example of an apparatus for controlling an x-ray device. The x-ray device is not shown in the drawing. The apparatus includes an introducer sheath 1 for introducing an intervention device 2 into a human blood vessel 3. The human blood vessel 3 may be a vein, for example. The intervention device 2 is a catheter, for example, that is to be introduced into the blood vessel 3. The apparatus also includes an acquisition facility 4, that is arranged directly on the introducer sheath 1 and may be used to monitor the introduction channel of the introducer sheath 1. The acquisition facility 4 may be arranged coaxially with the introducer sheath 1. In this case the intervention device 2 is firstly guided through the acquisition facility 4 and then immediately through the introducer sheath 1.

The acquisition facility 4 may be a device scanner, that is arranged or fastened directly on the introducer sheath 1. The device scanner functions magnetically, optically or by RFID technology. The direct arrangement of the acquisition facility 4 on the introducer sheath 1 provides that the intervention device 2, that is to be introduced into a blood vessel 3 of a patient for example, is guided automatically through the acquisition facility 4, for example the device scanner or directly past the same.

Figure 2:
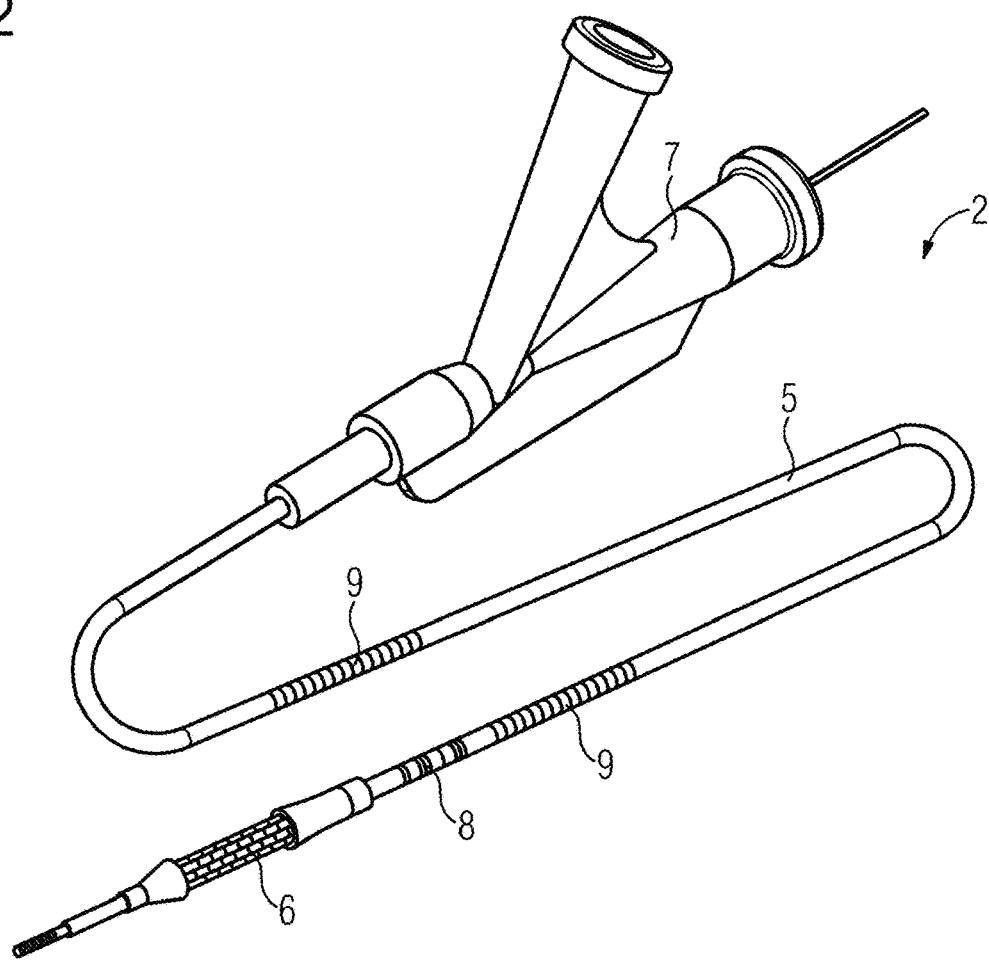
FIG. 2 depicts an intervention device with identification information and position information according to an embodiment.

FIG. 2 depicts an intervention device 2 in detail. The intervention device 2 is a catheter with a stent 6, for example. The stent 6 is located at the distal end of a catheter tube 5, i.e. at the catheter tip. A control lever 7 is arranged at the proximal end of the catheter tube 5. A code 8, to which an item of identification information is assigned, is likewise located on the catheter tip. The code 8 for identifying the intervention device 2 is located on the catheter tube 5 in the region of the catheter tip for example. In the present example in FIG. 2, the code 8 is located directly behind the stent 6. The code 8 may however also be located in front thereof.

Each intervention device may bear a code of this type for identification. The code 8 may be read radially from all sides. A barcode on a magnetic or optical basis may be used. Corresponding magnetic or optical rings at various distances in the axial direction may represent a barcode that may be read from all sides. The code 8 may however also be any other code, for example a QR code, color code, cipher code or suchlike. The acquisition facility 4 or the device scanner automatically registers the intervention device 2 or a type and controls the x-ray device as a function thereof and selects an identified organ program, for example.

In addition to the code for the identification, the intervention device 2 may additionally bear a code for the position determination, for example, positioning markers 9 that are arranged periodically along the axis of the catheter tube 5. The positioning marker 9 may include magnetic or optical rings with an axial distance of a millimeter or less. The positioning markers 9 are registered during the intervention by the device scanner to identify the position of the intervention device 2 in the blood vessel 3, for example. An additional functionality is produced as a result. With the position measurement, the navigation phase of the intervention device 2, e.g. the stent 6, may be differentiated from the application phase. In the navigation phase, the introduction depth of the intervention device 2 is minimal, whereas in the application phase the intervention device 2 is introduced deeply. A special relation between the introduction depth and the introduction depth of other devices such as the catheter or guide wires may however also be checked. If the introduction depth of the intervention device 2 is measured, an organ program that results in a low dose may be selected in the navigation phase and an organ program that result in a high resolution may be selected in the application phase.

Furthermore, the device scanner or the acquisition facility 4 may determine the speed of the intervention device 2 and the direction of movement. Image processing parameters may be set on the basis of the speed and the direction of movement. For example, the parameters of a temporal averaging algorithm may be selected dependently hereupon. A higher temporal averaging may be carried out with a slow movement, while a lower temporal averaging is carried out with a rapid movement. With more complex marker forms and more highly developed scanners, rotations of the intervention device 2 (e.g. of the guide wire) may also be determined.

The device scanner may be used for accurate measurements of the distances in the interior of a blood vessel 3 with the aid of guide wires. The user may mark a specific position of the wire tip by actuating a system button "set zero position" for example. The distances (introduction depths of the wire) relative to this position may be shown on an operation monitor. The distance measurements are more accurate than typical techniques that use stored x-ray images. Imaging techniques require the calibration of the vascular position and the vascular angle with respect to the detector plane. Both factors reduce the accuracy of the distance measurements. The method for measuring the distances based on the scanning of position markers on the device is not affected by such inaccuracies. Furthermore, the method is quicker. Exact distance measurements are also significant to the diagnosis and result in clinical decisions such as the choice of the stent.

Two alternative technologies are described in more detail below that use a barcode and a corresponding scanner or RFID technology.

A magnetic identifier of the guide wire or of the catheter may take place and a magnetic head scanner may be used. The functionality of the magnetic acquisition with guide wires and catheters may be realized in that magnetic powder is mixed into the casing of the wire or into the catheter material. The magnetic powder may then be magnetized and encoded locally accordingly with a magnetic head technology, such as is used with magnetic strip recorders. The expected bit density may be 10 bit per mm or higher. A miniaturized magnetic head may read the magnetic barcode, similarly to the position marker stored on the intervention device 2.

If a number of devices are introduced into the vessel or into the bloodstream, only one single one is moved by the operator at any one point in time. The magnetic head may only read the information from a moving intervention device. To reduce the possibility of misidentification of the device marker when a number of devices is used simultaneously, each type or each group of devices (e.g. guide wires, catheter, microcatheter) may include a single marker structure (bit sequence) of this type.

An optical barcode and laser barcode scanner may be used. The barcode may be painted or printed by transparently coating the guide wire or catheter. The catheters may be optically transparent and include semitransparent barcodes, so that when a number of intervention devices are introduced simultaneously, all intervention devices or their encodings may be acquired optically. The semitransparent optical markers may provide for the acquisition of several devices. Unique marker structures also allow the unique identification of position markers.

Miniaturized RFID components may be used. The intervention device includes a miniaturized RFID chip and an antenna in the vicinity of its tip. A corresponding scanner on the introducer sheath reads out the identification information. In some examples, magnet technology is superior to optical technology, since with the latter the transparency of the catheters and guide wires or coatings is limited. Both technologies allow the simultaneous identification of a number of devices and the positions, however.

Figure 3:
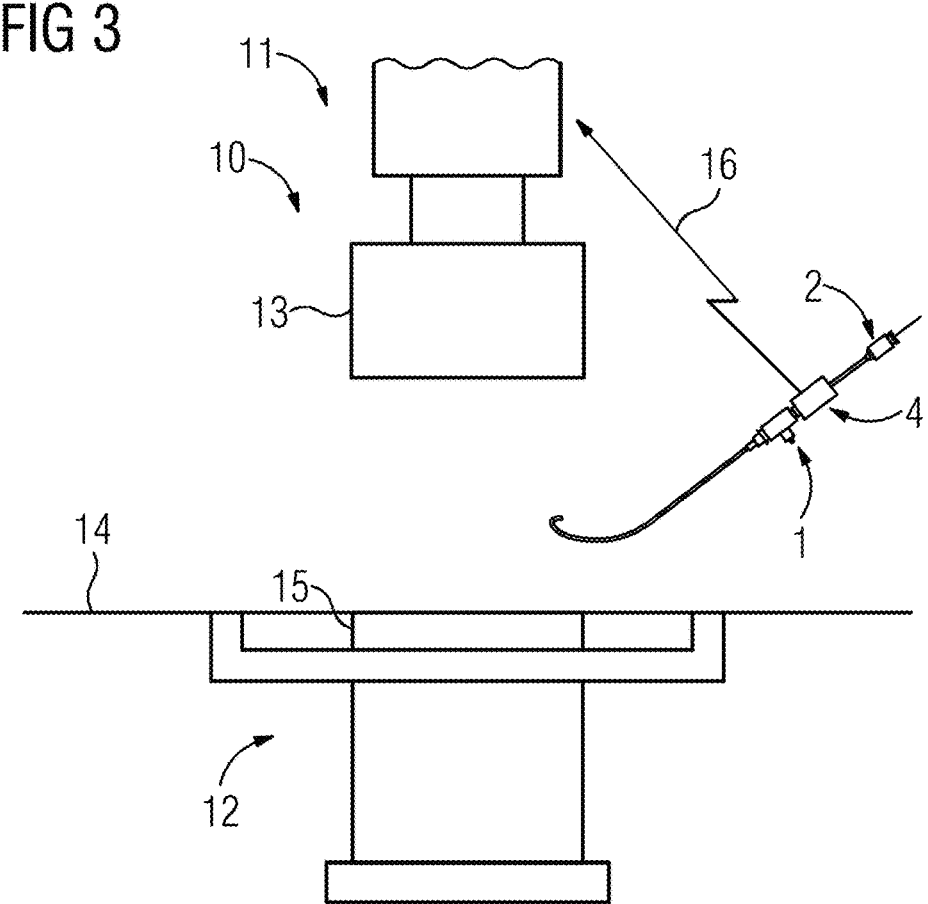
FIG. 3 depicts an x-ray device with the apparatus according to an embodiment.

FIG. 3 depicts a schematic representation of an x-ray device 10. The x-ray device 10 includes a radiation unit 12 and a receiving unit 11. The radiation unit 12 may include a housing 15, in which an x-ray source (not depicted) and a control facility (not depicted) is accommodated to control the x-ray source and is combined with a patient couch 14. The receiving unit 11 may include a housing 13 and therein a detector unit (not depicted) for detecting the x-ray radiation. The apparatus with the introducer sheath 1, the acquisition facility 4 and the optional intervention device 2, is in a data connection 16 with the remaining x-ray device 10, for example, the control facility. The data connection 16 may be wireless or wired. The power supply to the acquisition facility 4 may be carried out independently with the aid of a battery, or by cable or also wirelessly by the control unit of the x-ray device 10. The intervention device 2 may be acquired individually or at least by type by the acquisition facility 4 and observed by the radiation unit 12 and the receiving unit 11.

Figure 4:
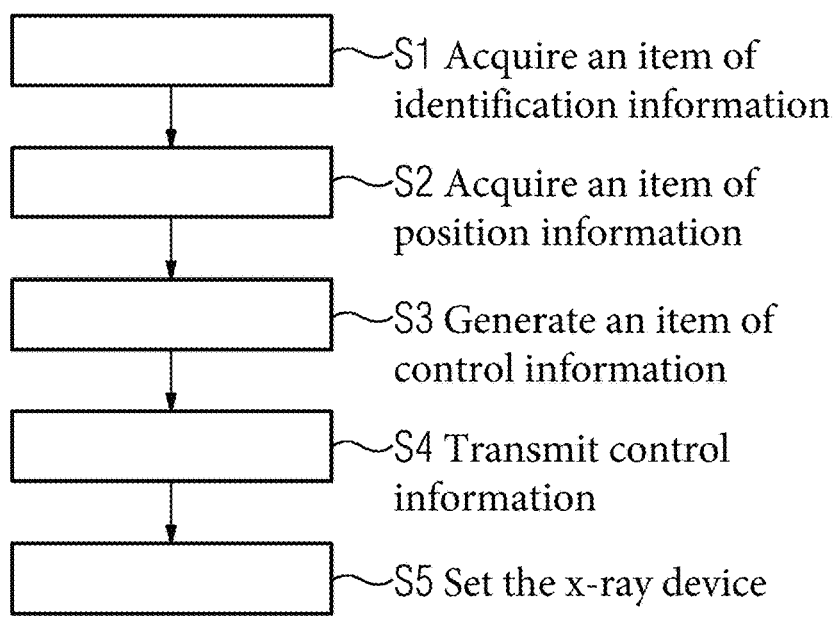
FIG. 4 depicts a schematic block diagram of a method for controlling an x-ray device according to an embodiment.

In conjunction with FIG. 4, one example of a method is depicted. In a first step S1, an item of identification information of the intervention device 2 is acquired optically, magnetically, or via RFID for example. Optionally an item of position information of the intervention device 2 is likewise acquired in a subsequent step S2 magnetically, optically, or in other ways for example (e.g. contactlessly). The position information may be acquired as a function of the time, as a result of which it is possible to determine the speed of the intervention devices and where applicable also the direction of movement of the intervention device.

In step S3, an item of control information is generated for the x-ray device 10 from the acquired or obtained information. This control information may be identical to the acquired information or obtained by a preprocessing of the acquired information.

In a fourth step S4, the control information is transmitted from the acquisition facility to the control facility of the x-ray device 10, for example. It is used in step S5 to set the x-ray device 10. The control information may be used to set individual exposure or display parameters or select entire organ programs.

The x-ray device or system (e.g. angiography system) may automatically identify the device introduced into the vessel and also where applicable, the introduction depth and the speed and direction of the device movement. The optimal organ program may be selected on the basis of the parameters, for example that provides the visibility of the device and at the same time what is known as ALARA working conditions. The user does not have to interact with the system to select the organ program. As a result, time, and attention may be saved.

The user may determine distances within the vessel quickly and accurately. Furthermore, a number of devices may be detected at the same time and the positions (penetration depth) measured independently of one another. This may apply to catheters, guide wires, and stents with the application systems.

Since the device scanner is fixed directly on the introducer sheath, for example, all intervention devices may be automatically scanned and registered if the intervention devices are introduced into the bloodstream. advantage may include in the registration and the depth measurement carried out with the aid of a barcode that is positioned on the device tip. Advantages also then result when series of thin markers are provided along the entire length of the intervention device for position acquisition purposes.

Embodiments provide the intervention device to be used in a user-friendly manner with its dedicated organ program, or even a series of organ programs that are adjusted to different clinical situations. The user may not interact for longer with the system in order to select the optimal organ program.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. An apparatus for controlling an x-ray device, the apparatus comprising:
   an intervention device:
   an introducer sheath configured to introduce the intervention device into a blood vessel; and
   an acquisition facility configured to automatically acquire identification information of the intervention device and to generate a corresponding item of control information for the x-ray device;
   wherein the acquisition facility is arranged directly on the introducer sheath.

2. The apparatus of claim 1, wherein the identification information is encoded on a distal end region of the intervention device.

3. The apparatus of claim 1, wherein the identification information is encoded on the intervention device using an RFID code, and the acquisition facility is configured to acquire the RFID code via RFID technology.

4. The apparatus of claim 1, wherein the identification information is attached to the intervention device by a magnetic code, and the acquisition facility is configured to acquire the magnetic code magnetically.

5. The apparatus of claim 1, wherein the identification information is attached to the intervention device by an optical code, and the acquisition facility is configured to acquire the optical code optically.

6. The apparatus of claim 5, wherein the acquisition facility further comprises a laser scanner configured to acquire the optical code on the intervention device.

7. The apparatus of claim 1, wherein the acquisition facility is further configured to acquire at least one position marker of the intervention device and to generate the control information as a function of the at least one position marker.

8. The apparatus of claim 7, wherein the acquisition facility is further configured to determine at least one of a position, a speed, or a direction of a movement of the intervention device to generate the control information based on the at least one position marker.

9. The apparatus of claim 1, wherein the intervention device comprises at least one of a catheter, a guide wire, a stent, or a surgical instrument.

10. The apparatus of claim 1, further comprising:
    an optical code attached to the intervention device, wherein the intervention device is optically transparent at least in one region, and the optical code attached to the intervention device includes a lower transparency compared with the one region.

11. A method for controlling an x-ray device, the method comprising:
    automatically acquiring identification information of an intervention device from an introducer sheath configured to introduce the intervention device into a blood vessel; and
    generating an item of control information for the x-ray device that corresponds to the identification information.

12. The method of claim 11, wherein automatically acquiring the identification information of the intervention device further comprises:
    acquiring at least one of a position, a speed, or a direction of a movement of the intervention device by the introducer sheath; and
    generating the item of the control information for the x-ray device is carried out as a function of the position, the speed, or the direction of movement.

13. The method of claim 12, further comprising:
    selecting an organ program from a plurality of organ programs in the x-ray device as a function of the item of the control information.

14. The method of claim 13, wherein selecting the organ program from the plurality of organ programs in the x-ray device comprises:
    automatically selecting an organ program with a lower x-ray dose from the plurality of organ programs if the speed exceeds a threshold value.

15. The method of claim 11, further comprising:
setting an exposure parameter or a display parameter of the x-ray device as a function of the item of the control information.

16. The method of claim 11, further comprising:
acquiring a position of the intervention device as a function of a zero position and a relative position of the intervention device relative to the zero position on the x-ray device.

17. The method of claim 11, wherein the identification information is encoded in a magnetic code.

18. The method of claim 11, wherein the identification information is encoded in an RFID code.

19. The method of claim 11, wherein the identification information is encoded in an optical code.

* * * * *